United States Patent [19]

Enzo

[11] Patent Number: 4,804,362
[45] Date of Patent: Feb. 14, 1989

[54] EAR CLEANING STICK PROVIDED WITH EAR CLEANING PORTIONS INCLUDING A DOUBLE STOP ABUTMENT

[76] Inventor: Lotti Enzo, Via Ostiglia, 8, 46100 Mantova, Italy

[21] Appl. No.: 138,293

[22] Filed: Dec. 28, 1987

[30] Foreign Application Priority Data

Sep. 25, 1987 [IT] Italy ............................. 22434/87[U]

[51] Int. Cl.4 ........................................... A01M 35/00
[52] U.S. Cl. ..................................................... 604/1
[58] Field of Search ..................... 604/1; 15/210 R; 128/152

[56] References Cited

U.S. PATENT DOCUMENTS

| 982,232 | 1/1911 | Bartholomew | 604/1 |
| 2,987,063 | 6/1961 | Glickston | 604/1 |
| 3,800,791 | 4/1974 | Visor | 128/152 |

FOREIGN PATENT DOCUMENTS 0237589 9/1987 European Pat. Off. ............... 604/1

Primary Examiner—Stephen C. Pellegrino
Attorney, Agent, or Firm—Bucknam and Archer

[57] ABSTRACT

The stick comprises, at one or both ends thereof, a shaped cotton flock including an essentially cylindrical portion having a rounded point and two projecting disc-like portions of different diameters.

1 Claim, 1 Drawing Sheet

U.S. Patent  Feb. 14, 1989  4,804,362

EAR CLEANING STICK PROVIDED WITH EAR CLEANING PORTIONS INCLUDING A DOUBLE STOP ABUTMENT

BACKGROUND OF THE INVENTION

The present invention relates to an ear cleaning stick, provided with cleaning portions including a double stop abutment.

As is known there are presently commercially available ear cleaning sticks which are specifically designed for removing earwax from the ear duct.

These ear cleaning sticks generally comprise a substantially semirigid stick rod firmly supporting, at one or both ends thereof, a substantially ovoidal shape cotton flock.

The end portion of the stick rod having said cotton flock is introduced, for cleaning purposes, into the ear duct and slowly rotated to remove the earwax usually coating the inner wall of the ear duct.

This operation, on the other hand, is to be carried out with a very high care and accuracy in order to not irritate the ear membrame because of the rubbing cleaning action exerted by the stick.

This fact is particularly true as an adult person tries to clean the ear duct of a child, in which case the adult person must operate without precise references and/or tactile feelings.

SUMMARY OF THE INVENTION

Accordingly, the main object of the present invention is to overcome the above mentioned drawbacks by providing an improved structure ear cleaning stick which can be used in a completely safe manner both by adult persons and by children.

Another object of the present invention is to provide an improved structure ear cleaning stick which is formed with means for preventing said stick from being excessively introduced into the ear duct.

Another object of the present invention is to provide an improved structure ear cleaning stick the cleaning portion of which includes geometrically different portions adapted for signalling to the user the insertion amount of the stick cleaning portion into the outer ear.

According to one aspect of the present invention the above mentioned objects, as well as yet other objects, which will become more apparent hereinafter, are achieved by an improved structure ear cleaning stick characterized in that it is provided, at one or both ends thereof, with a shaped cotton flock including, from the outside toward the inside thereof, an essentially cylindrical portion having a rounded point and two disc-like projecting portions of different diameters.

BRIEF DESCRIPTION OF THE DRAWINGS

Further characteristics and advantages of the improved structure ear cleaning stick according to the present invention will become more apparent hereinafter from the following description of a preferred embodiment thereof, which is illustrated, by way of an indicative but not limitative example, in the figures of the accompanying drawings, wherein.

DESCRIPTION OF THE PREFERRED EMBODIMENT

Figure 1:
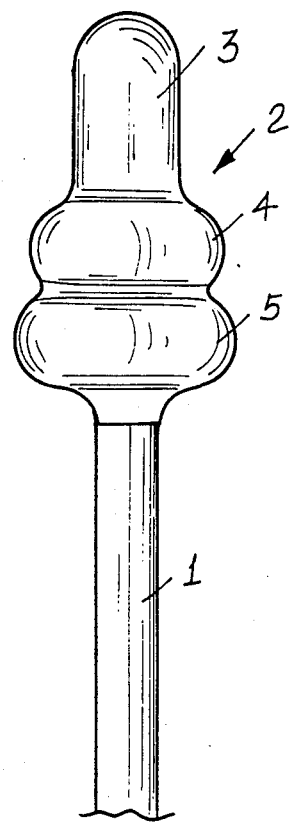
FIG. 1 is an enlarged view illustrating an end portion of the ear cleaning stick according to the present invention.
Figure 2:
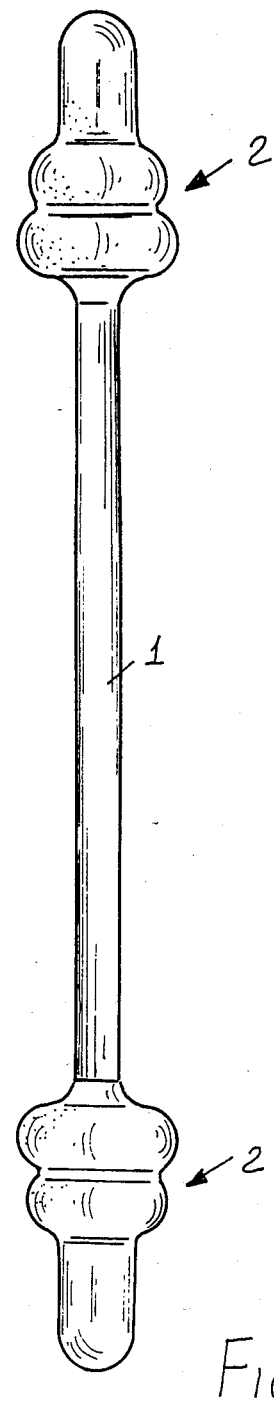
FIG. 2 is an outline view illustrating that same ear cleaning stick.

With reference to the figures of the accompanying drawings, the ear cleaning stick according to the present invention comprises a round cross-section stick rod 1, made of a suitable substantially flexible plastics material.

The stick rod is provided, at one or both ends thereof, with compacted shaped cotton flocks, generally indicated with 2.

More specifically, the mentioned cotton flocks 2 comprise a first portion 3 having a substantially cylindrical shape and a rounded point, provided for insertion into the ear duct.

This first portion 3 is followed by two other substantially disc-shaped portions 4 and 5, of different diameters, the edges of which have a convex cross-section.

In this connection it should be pointed out that the first disc-shaped portion has a width which has been specifically designed for defining a stop abutment adapted for preventing the first mentioned stick portion from being excessively introduced into at least the ear duct of a child.

The second disc-shaped portion, in turn, has a diameter which has been specifically designed for preventing the mentioned cleaning cylindrical portion from being excessively introduced into the ear duct of an adult person.

Thus, owing to the disclosed structural features, the ear cleaning stick according to the present invention can be safely used both by children and adult persons.

Infact the above disclosed disc-like portions are adapted for preventing the rounded point of the cylindrical cleaning portion of the cotton flock from contacting the ear membrane.

While the ear cleaning stick according to the present invention has been disclosed and illustrated with reference to a preferred embodiment thereof, it should be apparent that it is susceptible to several modifications and variations, all of which come within its spirit and the scope of the appended claims.

I claim:

1. An ear cleaning stick comprising, at one or both ends thereof, a shaped single compacted cotton flock including, from the outside toward the inside thereof, an essentially cylindrical rounded-point portion and two projecting disc-like portions of different diameters, wherein the edges of said two projecting disc-like portions have a convex cross-section and wherein the first of said two projecting disc-like portions is formed with a width adapted to define a a stop abutment for preventing said cylindrical rounded-point from being excessively introduced into the ear duct of a child, whereas the second of said projecting disc-like portions has a diameter designed for preventing said cylindrical rounded-point cleaning portion from being excessively introduced into the ear duct of an adult person.

* * * * *